(12) United States Patent
Leussler et al.

(10) Patent No.: US 11,940,521 B2
(45) Date of Patent: Mar. 26, 2024

(54) MULTI-CHANNEL PILOT TONE MOTION DETECTION

(71) Applicant: KONINKLIJKE PHILIPS N.V., Eindhoven (NL)

(72) Inventors: Christoph Gunther Leussler, Hamburg (DE); Christian Findeklee, Norderstedt (DE); Jan Jakob Meineke, Hamburg (DE); Peter Vernickel, Humburg (DE); Peter Koken, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 234 days.

(21) Appl. No.: 17/612,066

(22) PCT Filed: May 18, 2020

(86) PCT No.: PCT/EP2020/063748
§ 371 (c)(1),
(2) Date: Nov. 17, 2021

(87) PCT Pub. No.: WO2020/234207
PCT Pub. Date: Nov. 26, 2020

(65) Prior Publication Data
US 2022/0206098 A1 Jun. 30, 2022

(30) Foreign Application Priority Data
May 20, 2019 (EP) .................................... 19175293

(51) Int. Cl.
*G01R 33/56* (2006.01)
*A61B 6/00* (2006.01)
(Continued)

(52) U.S. Cl.
CPC ........ *G01R 33/56509* (2013.01); *A61B 6/037* (2013.01); *A61B 6/4417* (2013.01); *A61B 6/5264* (2013.01); *G01R 33/5673* (2013.01)

(58) Field of Classification Search
CPC .......... G01R 33/56509; G01R 33/5673; G01R 33/36; A61B 6/037; A61B 6/4417;
(Continued)

(56) References Cited

U.S. PATENT DOCUMENTS

2006/0244452 A1 11/2006 Den Boef
2010/0259261 A1 10/2010 Saes et al.
(Continued)

FOREIGN PATENT DOCUMENTS

DE 102008019862 A1 10/2009
EP 3413075 A1 12/2018
(Continued)

OTHER PUBLICATIONS

Schroeder et al "A Novel Method for Contact Free Cardiac Synchronization Using the Pilot Tone Navigator" Proc Intl. Soc. Mag. Reson Med 24 (2016).
(Continued)

*Primary Examiner* — G. M. A Hyder

(57) ABSTRACT

Disclosed is a medical system (100, 300, 500, 700) comprising: a memory (128) storing machine executable instructions (130); a processor (122) configured for controlling the medical system; and a pilot tone system (106). The pilot tone system comprises a radio frequency system (108) comprising multiple transmit channels (110) and multiple receive channels (112). The multiple transmit channels are configured for each transmitting unique pilot tone (132) signals via multiple transmit coils. The multiple receive channels are configured for receiving multi-channel pilot tone data (134) via multiple receive coils. Execution of the machine execut-
(Continued)

able instructions causes the processor to: transmit (200) multi-channel pilot tone signals by controlling at least a portion of the multiple transmit channels to transmit the unique pilot tone signals; acquire (202) multi-channel pilot tone data (134) by controlling at least a portion of the multiple receive channels to receive the multi-channel pilot tone data; and determine (204) a motion state (136) of the subject using the multi-channel pilot tone data.

19 Claims, 13 Drawing Sheets

(51) Int. Cl.
    *A61B 6/03*         (2006.01)
    *G01R 33/565*    (2006.01)
    *G01R 33/567*    (2006.01)

(58) Field of Classification Search
    CPC ..... A61B 6/5264; A61B 6/032; G01S 13/003; G01S 13/88
    See application file for complete search history.

(56) References Cited

U.S. PATENT DOCUMENTS

| | | | |
|---|---|---|---|
| 2015/0002331 | A1 | 1/2015 | Allmendinger et al. |
| 2015/0207653 | A1 | 7/2015 | Oppelt et al. |
| 2015/0320342 | A1 | 11/2015 | Biber et al. |
| 2016/0103195 | A1 | 4/2016 | Zehlsdorff et al. |
| 2017/0160367 | A1 | 6/2017 | Schroter et al. |
| 2018/0353139 | A1 | 12/2018 | Speier et al. |
| 2018/0353140 | A1* | 12/2018 | Speier ................ G01R 33/5673 |
| 2019/0361082 | A1* | 11/2019 | Hess .................. G01R 33/5673 |
| 2020/0284863 | A1* | 9/2020 | Leussler .......... G01R 33/34007 |
| 2020/0375463 | A1 | 12/2020 | Hess et al. |

FOREIGN PATENT DOCUMENTS

| | | |
|---|---|---|
| EP | 3413076 A1 | 12/2018 |
| EP | 2018173009 A1 | 11/2019 |
| WO | 2018173009 A1 | 9/2018 |

OTHER PUBLICATIONS

International Search Report and Written Opinion from PCT/EP2020/063748 dated Nov. 26, 2020.

P. Speier et al. "PT-Nav: A Novel Respiratory Navigation Method for Continuous Acquisition Based on Modulation of a Pilot Tone in the MR-Receiver", Proc. ESMRMB 128:97-98, 2015.

L. Schroeder et al. "Two-Dimensional Respiratory-Motion Characterization for Continuous MR Measurements Using Pilot Tone Navigation". In Proc. Intl. Soc. Mag. Reson.Med. 24:3103, 2016.

A. Hyvärinen, "Fast and robust fixed-point algorithms for independent component analysis", IEEE Transactions on Neural Networks, vol. 10, No. 3, pp. 626-634.

C. I. O. Brookes et al. "Myocardial contractility is not constant during spontaneous atrial fibrillation in patients", Circulation, 98:1762-1768,1998.

Mario Bacher et al, "Pilot Tone Navigation Enables Contactless Prospective Cardiac Triggering: Initial Volunteer Results for Prospective Cine" Proc. Intl. Soc. Mag. Reson. Med. 26 (2018) p. 2960.

Peter Speier, "Separation and Quantification of Head Motion Modes by Pilot Tone Measurements", Proc. Intl. Soc. Mag. Reson. Med. 26 (2018) p. 4101.

David Rigi, "Tracking Respiratory Motion Throughout Arbitrary MRI Sequences via Pilot Tone Navigation", Proc. Intl. Soc. Mag. Reson. Med. 26 (2018)p. 4108.

Mario Bacher, Master Thesis Cardiac Triggering Based on Locally Generated Pilot-Tones in a Commercial MRI Scanner: A Feasibility Study (2017).

Pfanner et al "Monitoring Respiratory Motion Using Continuous Wave Doppler Radar in a Near Field Multi Antenna Approach" 2012.

Chen Qin, Jo Schlemper, Jose Caballero, Anthony N. Price, Joseph V.Hajnal, Daniel Rueckert, Convolutional Recurrent Neural for Dynamic MR Image Reconstruction, IEEE Transaction on Medical Imaging, vol. 38, Issue: 1, Jan. 2019, pp. 280-290.

M. Bacher et al. "Retrospective Evaluation of Pilot Tone Based Cardiac Trigger Quality in a Volunteer Cohort", Book of Abstracts ESMRMB 2017 30:360-361, 2017.

* cited by examiner

MULTI-CHANNEL PILOT TONE MOTION DETECTION

CROSS REFERENCE TO RELATED APPLICATIONS

This application is a U.S. national phase application of International Application No. PCT/EP2020/063748 filed on May 18, 2020, which claims the benefit of EP Application Serial No. 19175293.0 filed on May 20, 2019 and is incorporated herein by reference.

FIELD OF THE INVENTION

The invention relates to tomographic medical imaging, in particular to the detection of subject motion using pilot tones.

BACKGROUND OF THE INVENTION

In tomographic medical imaging techniques such as magnetic resonance imaging, x-ray computed tomography, positron emission tomography, and others data is acquired from a subject over a period of time and used to reconstruct a medical image. This enables physicians or other health care professionals to accurately image a subject's internal anatomy. A disadvantage of these techniques is that the subject can move during the acquisition of the medical imaging data, which can lead to the addition of artifacts in the medical image.

A variety of techniques exist for correcting or compensating for subject motion. One technique is the pilot tone technique. In magnetic resonance imaging, a transmit coil is used to transmit a radio frequency signal and another receive coil is used to receive this signal. The amount of coupling between the subject and these two coils determines the strength of the received signal. Motions such as heart motion, breathing, and bulk body motion can be detected in a change in the signal strength.

United States patent application publication US20150320342A1 discloses a magnetic resonance device includes a radiofrequency unit that includes a radiofrequency antenna, at least one radiofrequency line and at least one radiofrequency injection point. Radiofrequency signals are transferred to the radiofrequency antenna by the at least one radiofrequency line and are coupled into the radiofrequency antenna at the at least one radiofrequency injection point. The magnetic resonance device also includes a patient receiving zone that is at least partially enclosed by the radiofrequency antenna, and a motion detection unit for detecting a movement of a patient that may be positioned within the patient receiving zone. At least one radiofrequency line includes at least one injection element by which at least one motion detection signal of the motion detection unit is coupled into the radiofrequency line.

SUMMARY OF THE INVENTION

The invention provides for a medical system, a computer program product, and a method in the independent claims. Embodiments are given in the dependent claims.

Embodiments of the invention may provide for an improved pilot tone system. This may be accomplished by using multiple transmit channels and multiple receive channels. The multiple transmit channels may be used to transmit a multi-channel pilot tone signal comprised of unique pilot tone signals. The multiple receive channels receive these signals as multi-channel pilot tone data. This provides much more information that conventional pilot tone systems. In the framework of the present invention, the pilot tone system is based on transmission of the pilot tone signal as an electromagnetic signal in the radio frequency range of e.g. 40-400 MHz. The pilot tone signal is transmitted in a continuous wave (cw) mode and the pilot tone data are due to impedance response to the transmitted pilot tone signal. This response is represented by the changes in amplitude and phase of the pilot tone data relative to that of the transmitted pilot tone signal. That is the pilot tone data represent a frequency domain response to the pilot tone signal and spectrally resolved information is carried by the pilot tone data.

In one aspect the invention provides for a medical system. The medical system comprises a memory which stores machine-executable instructions. The medical system further comprises a processor configured for controlling the medical system. The medical system further comprises a pilot tone system. The pilot tone system comprises a radio-frequency system. The radio-frequency system comprises multiple transmit channels and multiple receive channels. The multiple transmit channels are configured for each transmitting unique pilot tone signals via multiple transmit coils. The multiple receive channels are configured for receiving pilot tone data via the multiple receive coils. The multiple receive coils may be configured for receiving the unique pilot tone signals.

The pilot tone data are the electrical signals generated in the multiple receive channels by the unique pilot tone signals. Execution of the machine-executable instructions causes the processor to transmit multi-channel pilot tone signals by controlling at least a portion of the transmit channels to transmit the unique pilot tone signals. Execution of the machine-executable instructions further causes the processor to acquire multi-channel pilot tone data by controlling at least a portion of the multiple receive channels to receive the multi-channel pilot tone data. Execution of the machine-executable instructions further causes the processor to determine a motion state of the subject using the multi-channel pilot tone data.

The motion state may be descriptive of periodic motion of the subject such as breathing or heartbeat and also in other examples it may be descriptive of gross or bulk motion of the subject. This embodiment may be beneficial because it may be useful in monitoring the position or motion of a subject during a medical procedure such as a tomographic imaging procedure.

In another embodiment the radio-frequency system is configured for encoding each of the unique pilot tone signals using frequency encoding.

In another embodiment the radio-frequency system is configured for encoding each of the unique pilot tone signals using phase encoding.

In another embodiment the radio-frequency system is configured for encoding each of the unique pilot tone signals using complex modulation.

In another embodiment the radio-frequency system is configured for encoding each of the unique pilot tone signals using CDMA encoding.

In another embodiment the motion state of the subject is any one of the following: a subject motion location; a motion vector; a subject motion classification; a breathing state; a heart motion state; a translation vector descriptive of at least a portion of the subject; a rotation descriptive of at least a portion of the subject; and combinations thereof. This embodiment may be beneficial because these are all various steps and motions which may be tracked using the multi-channel pilot tone system.

In another embodiment execution of the machine-executable instructions further causes the processor to determine the motion state by using a recurrent neural network configured for receiving the multi-channel pilot tone data and the unique pilot tone signals and for outputting the motion state. The unique pilot tone signals are essentially the signals transmitted by the multiple transmit channels and the multi-channel pilot tone data is the data which is received by the multiple receive channels. These may be input into a trained recurrent neural network to analyze the time-dependent signals from both. This may be useful in outputting the motion state.

In another embodiment the machine-executable instructions causes the processor to determine the motion state by detecting the distance between the subject and each of the multiple receive coils. The multiple receive coils may be offset a distance from the subject. The strength of the signal may then be used to measure the distance between the subject and individual receive coils. This enables the use of a simple model to map the location of the subject.

In another embodiment execution of the machine-executable instructions causes the processor to determine the motion state using a digital filter. In a pilot tone system it is relatively straight forward to detect periodic motion. For example, motion that is due to the heart has a frequency component which is similar to the frequency of the beating heart. A digital filter may then be used to isolate the signal from a heartbeat. Likewise, the motion of the subject due to breathing will also cause a frequency component which is similar to the breathing rate of a subject. The digital filter therefore simply enables the determination of certain types of periodic motion.

In another embodiment execution of the machine-executable instructions further causes the processor to determine the motion state using principle component analysis. This machine learning technique is effective in detecting various types of signals which may be indicative of motion.

In another embodiment the medical system further comprises a magnetic resonance imaging system.

In another embodiment the magnetic resonance imaging system further comprises a magnetic resonance imaging coil. The magnetic resonance imaging coil comprises the multiple pilot tone transmit coils and the multiple receive coils. This embodiment may be beneficial because the pilot tone transmit coils and multiple receive coils may be easily integrated into the magnetic resonance imaging coil.

In another embodiment the magnetic resonance imaging system is further configured for acquiring magnetic resonance imaging data within an imaging frequency range. The multiple transmit channels are configured for transmitting the unique pilot tone signals outside of the imaging frequency range. This may be beneficial because then the electromagnetic signals used by the pilot tone signal will not interfere with the acquisition of magnetic resonance imaging data. This for example may enable both the acquisition of magnetic resonance imaging data as well as operating the pilot tone signal simultaneously.

In another embodiment the memory further contains pulse sequence commands configured for controlling the magnetic resonance imaging system to acquire magnetic resonance imaging data. Execution of the machine-executable instructions further causes the processor to control the magnetic resonance imaging system with the pulse sequence commands to acquire the magnetic resonance imaging data. Execution of the machine-executable instructions causes the processor to perform the following during controlling the magnetic resonance imaging system with the pulse sequence commands: transmitting the multi-channel pilot tone signals; acquiring the multi-channel pilot tone data; and determining the motion state of the subject using the multi-channel pilot tone data. This embodiment is beneficial because the motion state determined from the pilot tone system may be used to either simultaneously control the magnetic resonance imaging system's acquisition and/or to later correct magnetic resonance imaging data for motion.

In another embodiment execution of the machine-executable instructions further causes the processor to determine a current gradient pulse frequency using the pulse sequence commands. The current gradient pulse frequency is the frequency at which the gradient coils are currently oscillating. Execution of the machine-executable instructions further cause the processor to detect subject motion with a periodicity within a predetermined range of the current gradient pulse frequency using motion state derived from the multi-channel pilot tone data. Execution of the machine-executable instructions further causes the processor to provide a peripheral nerve stimulation warning signal if the subject motion is detected.

The gradient coils in the magnetic resonance imaging system may generate currents or electrical fields in the subject. This can cause what is known as peripheral nerve stimulation and cause muscular tissue of the subject to move. In this embodiment the frequency at which the gradient pulses are generated is compared to the multi-channel pilot tone data. If a frequency component above a predetermined threshold is determined then this may be indicative of the peripheral nerve stimulation of the subject being examined. This frequency may also be compared or correlated to the actual gradient signals. This may be used to further increase the confidence that peripheral nerve stimulation is occurring.

In another embodiment execution of the machine-executable instructions further causes the processor to select alternative pulse sequence commands if the peripheral nerve stimulation warning is provided. For example, the medical system may have a set of different pulse sequence commands which can be used and if peripheral nerve stimulation is detected using one the system may select the alternative pulse sequence commands.

In another embodiment execution of the machine-executable instructions further causes the processor to modify the pulse sequence commands if the peripheral nerve stimulation warning is provided. For example, the processor may cause the frequency or strength of various gradient pulses to be modified.

In another embodiment execution of the machine-executable instructions further cause the processor to cancel execution of the pulse sequence commands if the peripheral nerve stimulation warning signal is provided. For example, if the peripheral nerve stimulation warning signal is above a certain critical or dangerous threshold the system may automatically terminate acquisition of the magnetic resonance imaging data.

The pilot tone system further comprises the multiple transmit coils and the multiple receive coils.

In another embodiment the medical system further comprises a tomographic imaging system configured for acquiring tomographic imaging data from a subject within an imaging zone. Execution of the machine-executable instructions further causes the processor to control the tomographic imaging system to acquire the tomographic imaging data.

Execution of the machine-executable instructions causes the processor to perform the following during controlling the tomographic imaging system to acquire the tomographic imaging data; transmit the multi-channel pilot tone signals; acquire the multi-channel pilot tone data; and determine the motion state of the subject using the multi-channel pilot tone data. This embodiment may be beneficial because using the pilot tone may be applied to other imaging modalities besides just magnetic resonance imaging.

In another embodiment execution of the machine-executable instructions further causes the processor to reconstruct a medical image using the tomographic imaging data. Execution of the machine-executable instructions further causes the processor to correct the reconstruction of the medical image using the motion state of the subject. For example, if the motion state or position of the subject is known, this may aid in reconstructing the medical image to compensate for the motion of the subject.

In another embodiment the tomographic imaging system is a positron emission tomography system.

In another embodiment the tomographic imaging system is a single-photon emission tomography system.

In another embodiment the tomographic imaging system is an X-ray computer tomography system.

In another embodiment the tomographic imaging system comprises a subject support for supporting at least a portion of the subject in the imaging zone. The at least a portion of the multiple transmit coils and at least a portion of the multiple receive coils are integrated into the subject support. This may be beneficial because it may provide for an effective means of integrating a pilot tone signal into a tomographic imaging system that is different than a magnetic resonance imaging system.

In one aspect the invention provides for a computer program product comprising machine-executable instructions for execution by a processor controlling a medical system. The medical system comprises a pilot tone system. The pilot tone system comprises a radio-frequency system comprising multiple transmit channels and multiple receive channels. The multiple transmit channels are configured for each transmitting unique pilot tone signals via multiple transmit coils. The multiple receive channels are configured for receiving multi-channel pilot tone data via the multiple receive coils. Execution of the machine-executable instructions causes the processor to transmit the multi-channel pilot tone signals by controlling at least a portion of the multiple transmit channels to transmit the unique pilot tone signals.

Execution of the machine-executable instructions further causes the processor to acquire multi-channel pilot tone data by controlling at least a portion of the multiple receive channels to receive the multi-channel pilot tone data. Execution of the machine-executable instructions further causes the processor to determine a motion state of the subject using the multi-channel pilot tone data.

In another aspect the invention provides for a method of operating a medical system. The medical system comprises a pilot tone system. The pilot tone system comprises a radio-frequency system comprising multiple transmit channels and multiple receive channels. The multiple transmit channels are configured for each transmitting unique pilot tone signals via multiple transmit coils. The multiple receive channels are configured for receiving multi-channel pilot tone data via multiple receive coils. The method comprises transmitting the multi-channel pilot tone signals by controlling at least a portion of the multiple transmit channels to transmit the unique pilot tone signals. The method further comprises acquiring multi-channel pilot tone data by controlling at least a portion of the multiple receive channels to receive the multi-channel pilot tone data. The method further comprises determining a motion state of the subject using the multi-channel pilot tone data.

In an example a magnetic resonance imaging system comprises a memory storing machine-executable instructions and pulse sequence commands configured for controlling the magnetic resonance imaging system to acquire magnetic resonance imaging data. The magnetic resonance imaging system further comprises a processor configured for controlling the magnetic resonance imaging system. The magnetic resonance imaging system further comprises a pilot tone system. The pilot tone system comprises a radio-frequency system comprising at least one transmit channel and at least one receive channel. The multiple receive channels are configured for receiving pilot tone data via the at least one transmit channel.

Execution of the machine-executable instructions further causes the processor to transmit at least one pilot tone signal by controlling the at least one transmit channel. Execution of the machine-executable instructions further causes the processor to acquire the pilot tone data by controlling the at least one receive channel to receive the pilot tone data. Execution of the machine-executable instructions further causes the processor to determine a motion state of the subject using the pilot tone data. Execution of the machine-executable instructions further causes the processor to determine a current gradient pulse frequency using the pulse sequence commands. Execution of the machine-executable instructions further causes the processor to detect subject motion with the periodicity within a predetermined range of the current gradient pulse frequency using the pilot tone data.

Execution of the machine-executable instructions further causes the processor to provide a peripheral nerve stimulation warning signal if the subject motion is detected. There may also be a threshold to determine if the subject motion is above a certain critical level or predetermined motion level which would require intervention from an operator or a physician. The subject motion can also be detected by determining a correlation between the motion state of the subject and the current or actual gradient pulse being produced by the gradient coils of the magnetic resonance imaging system. This embodiment may be beneficial because it may provide for a means of automatically detecting if the subject has motion due to peripheral nerve stimulation. This may for example increase the safety of the magnetic resonance imaging system as well as be useful for improving image quality because motion of the subject is reduced.

In another embodiment execution of the machine-executable instructions further causes the processor to provide any one of the following if the peripheral nerve stimulation warning is provided: to select alternative pulse sequence commands, modify the pulse sequence commands, cancel execution of the pulse sequence commands, and display a visible or audible signal.

In another embodiment the magnetic resonance imaging system further comprises a magnetic resonance imaging coil. The magnetic resonance imaging coil comprises the at least one pilot tone transmit coil and the at least one receive coil. In another embodiment the magnetic resonance imaging system comprises a subject support and at least a portion of the at least one pilot tone transmit coil and at least one receive coil are integrated into the subject support.

In another embodiment the magnetic resonance imaging system is configured for acquiring magnetic resonance imaging data within an imaging frequency range. The multiple transmit channels are configured for transmitting the unique pilot tone signals outside of the image frequency range. This may be beneficial because the operation of the pilot tone system does not interfere with the acquisition of magnetic resonance imaging data.

In another embodiment the at least one transmit channel is multiple transmit channels.

In another embodiment the at least one receive channel is multiple receive channels.

In another embodiment the at least one transmit channel is a single transmit channel.

In another embodiment the at least one receive channel is a single receive channel.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two- or three-dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
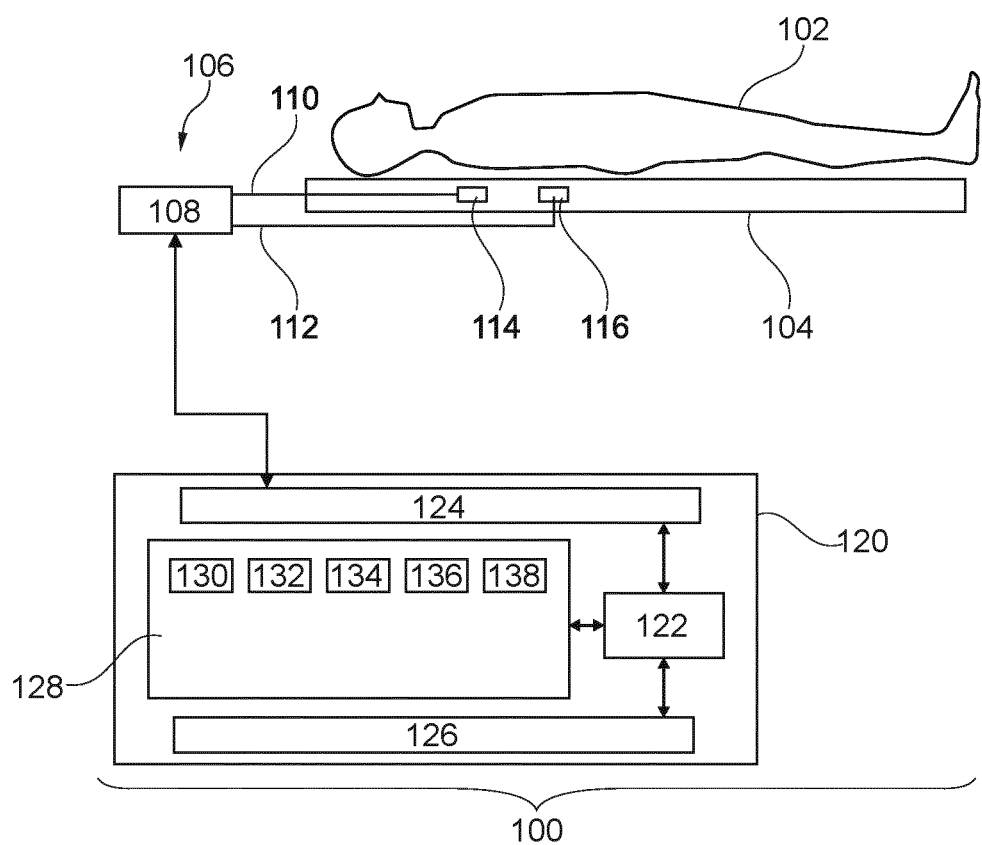
FIG. 1 illustrates an example of a medical system.

FIG. 1 illustrates an example of a medical system 100. The medical system 100 is shown as examining a subject 102. The subject 102 is shown as reposing on a subject support 104. The subject support 104 is optional. The medical system 100 comprises a pilot tone system 106. The pilot tone system has a radio-frequency system 108 with multiple transmit channels 110 and multiple receive channels 112. The multiple transmit channels 110 are connected to multiple transmit coils 114. The multiple receive channels 112 are connected to multiple receive coils 116. The medical system 100 is further shown as comprising a computer 120 that contains a processor 122. The processor 122 is intended to represent one or more processors.

The processor 122 may for example represent multiple processing cores as well as processors 122 distributed amongst multiple computer systems. The processor 122 is connected to a hardware interface 124 that enables the processor 122 to control other components of the medical system 100. The hardware interface 124 may for example also function as a network interface and enable the processor 122 to communicate with other processors and/or computer systems. The computer 120 is further shown as containing an optional user interface 126 that may for example be used by an operator to control the medical system 100. The computer 120 is further shown as containing a memory 128.

The memory 128 may be any combination of memory which is accessible to the processor 122. This may include such things as main memory, cached memory, and also non-volatile memory such as flash RAM, hard drives, or other storage devices. In some examples the memory 128 may be considered to be a non-transitory computer-readable medium.

The memory 128 is shown as containing machine-executable instructions 130. The machine-executable instructions 130 enable the processor 122 to control the operation and function of the medical system 100. The machine-executable instructions 130 may for example also enable the processor 122 to perform various data analysis and image processing techniques. The memory 128 is further shown as containing unique pilot tone signals 132 that have been constructed for each of the multiple transmit channels 110. The unique pilot tone signal 132 for example may be transferred via the processor 122 to the radio-frequency system 108 for transmission. The memory 128 is further shown as containing multi-channel pilot tone data 134. The multi-channel pilot tone data 134 is the digitized data recorded by the multiple receive channels 112. The transmit channels transmit the unique pilot tone signals 132 and this results in the receive channels receiving some portion of those signals. This is the multi-channel pilot tone data 134.

The combination of the unique pilot tone signals 132 results in multi-channel pilot tone signals which are collectively transmitted. The memory 128 is further shown as containing a motion state 136 that has been calculated using the multi-channel pilot tone data 134 and the unique pilot tone signals 132 or the multi-channel pilot tone signals. The motion state 136 may be calculated using a variety of different models for signal processing techniques. As one example the memory 128 is shown as containing a recurrent neural network 138. The recurrent neural network 138 receives the unique pilot tone signals 132 and the multi-channel pilot tone data 134 is input and then outputs the motion state 136.

In one example of FIG. 1, the components of the pilot tone system in integrated into the subject support also. For example, the pilot tone system could be completely contained within the subject support. This could for example enable the addition of a pilot tone system to a medical imaging system such as an MRI or an X-ray system by the use of the subject support. The subject support could also be used for different imaging techniques such as magnetic resonance imaging. A single subject support could be moved to different imaging system as well as different types of imaging systems.

Figure 2:
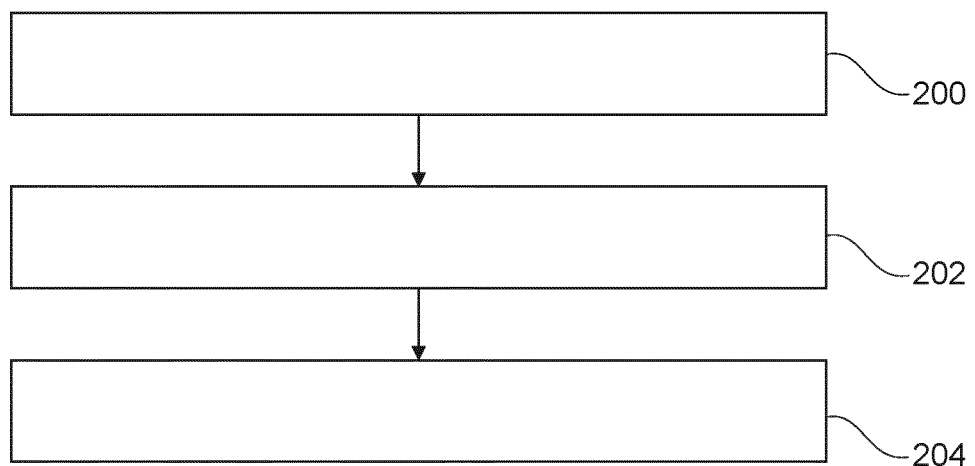
FIG. 2 shows a flow chart which illustrates a method of operating the medical system of FIG. 1.

FIG. 2 shows a flowchart which illustrates a method of operating the medical system 100 of FIG. 1. First in step 200, the multi-channel pilot tone signals 132 are transmitted by controlling at least a portion of the multiple transmit channels 110. The multi-channel pilot tone signals are the individual unique pilot tone signals 132 collectively. Next in step 202, the multi-channel pilot tone data 134 is acquired by controlling at least a portion of the multiple receive channels 112.

Finally, in step 204, the motion state 136 of the subject 102 is determined using the multi-channel pilot tone data 134. In the case of the recurrent neural network 138 likely both the multi-channel pilot tone data 134 and the individual unique pilot tone signals 132 would be input. In other cases, the motion state 136 can be determined from the multi-channel pilot tone data 134 alone. For example, the periodic breathing or heart motion of a subject 102 may cause the multi-channel pilot tone data 134 to have a frequency component which is equal to or about equal to the heart rate and/or breathing rate. The heart and/or breathing motion may therefore be determined by the multi-channel pilot tone data 134 alone.

Figure 3:
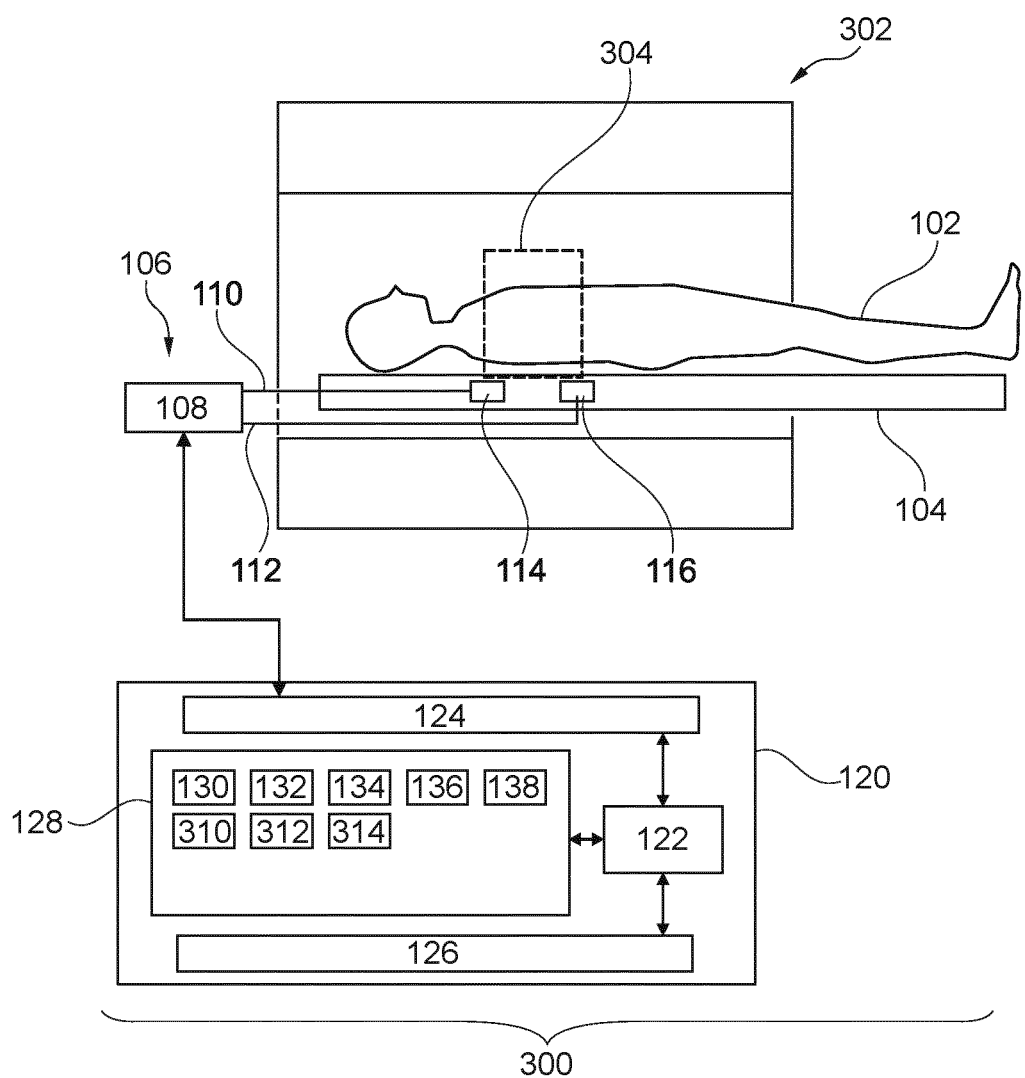
FIG. 3 illustrates a further example of a medical system.

FIG. 3 illustrates a further example of a medical system 300. The medical system 300 in FIG. 3 is similar to the medical system 100 in FIG. 1 except that the medical system 300 additionally comprises a tomographic imaging system 302. The tomographic imaging system may for example be a positron emission tomography system, a single photon emission tomography system or an X-ray computer tomography system. In this example the tomographic imaging system 302 has a cylindrical symmetry; however, this is not a requirement. The subject support 104 is shown as supporting a portion of the subject 102 within an imaging zone 304. The imaging zone 304 is a location in space where the tomographic imaging system 302 is able to acquire tomographic imaging data 312.

The memory 128 is further shown as containing control commands 310 that enable the processor 122 to control the tomographic imaging system 302 to acquire tomographic imaging data 312. The memory 128 is further shown as containing tomographic imaging data 312 that was acquired by controlling the tomographic imaging system 302 with the control commands 310. The memory 128 is further shown as containing a tomographic medical image 314 that was reconstructed from the tomographic imaging data 312. The multi-channel pilot tone data 134 may for example be acquired simultaneously with the tomographic imaging data 312. This enables various things which can be used to account for motion of the subject 102. For example, the multi-channel pilot tone data 134 and resulting motion state 136 can be used for gating the acquisition of the tomographic imaging data 312. In other examples the motion of the subject 102 can be determined in greater detail and the motion state 136 can be used during the reconstruction of the tomographic medical image 314.

Figure 4:
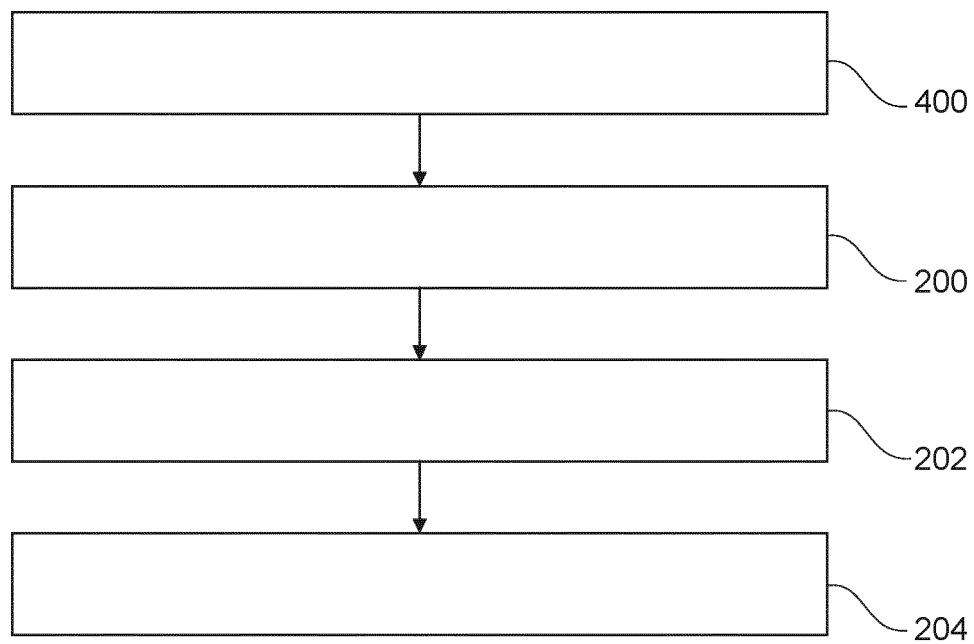
FIG. 4 shows a flow chart which illustrates a method of operating the medical system of FIG. 3.

FIG. 4 shows a flowchart which illustrates a method of operating the medical system 300 of FIG. 3. First in step 400 the processor 122 controls the tomographic imaging system 302 with the control command 310. Simultaneous with this, steps 200, 202 and 204 are performed as was illustrated in FIG. 2.

Figure 5:
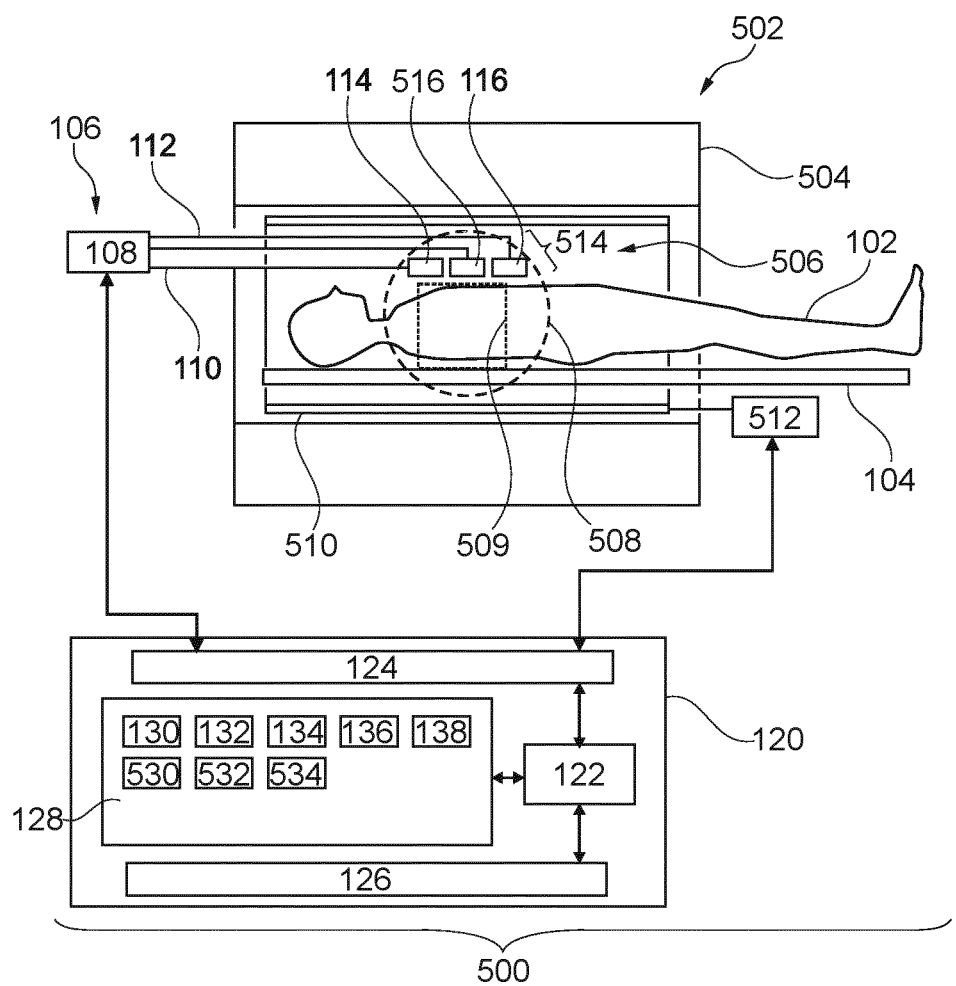
FIG. 5 illustrates a further example of a medical system.

FIG. 5 illustrates a further example of a medical system 500. The medical system in FIG. 5 is similar to the medical system 300 in FIG. 3 except the tomographic imaging system is specifically a magnetic resonance imaging system 502.

The magnetic resonance imaging system 502 comprises a magnet 504. The magnet 504 is a superconducting cylindrical type magnet with a bore 506 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 506 of the cylindrical magnet 504 there is an imaging zone 508 where the magnetic field is strong and uniform enough to perform magnetic resonance imaging. A region of interest 509 is shown within the imaging zone 508. The magnetic resonance data that is acquired typically acquired for the region of interest. A subject 102 is shown as being supported by a subject support 104 such that at least a portion of the subject 102 is within the imaging zone 508 and the region of interest 509.

Within the bore 506 of the magnet there is also a set of magnetic field gradient coils 510 which is used for acquisition of preliminary magnetic resonance data to spatially encode magnetic spins within the imaging zone 508 of the magnet 504. The magnetic field gradient coils 510 connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Within the bore 506 of the magnet 504 is a magnetic resonance imaging antenna 514. The magnetic resonance imaging antenna 514 is shown as comprising the multiple transmit coils 114 and the multiple receive coils 116. The magnetic resonance imaging antenna 514 also comprises a number of radio-frequency coils 516 which are used for performing the magnetic resonance imaging. The radio-frequency system 108 is also connected to the radio-frequency coil 516. The arrangement shown in FIG. 5 enables the acquisition of magnetic resonance imaging data simultaneous with the use of the pilot tone system. In other examples the radio-frequency coils 516 may also function as the multiple transceiver coils 114 and/or multiple receive coils 116.

The radio frequency coils 516 may also be referred to as a channel or antenna. The magnetic resonance antenna 514 is connected to a radio frequency system 108. The magnetic resonance antenna 514 and radio frequency system 108 may be replaced by separate transmit and receive coils and a separate transmitter and receiver. It is understood that the magnetic resonance antenna 514 and the radio frequency system 108 are representative. The magnetic resonance antenna 514 is intended to also represent a dedicated transmit antenna and a dedicated receive antenna. Likewise the system 516 may also represent a separate transmitter and receivers. The magnetic resonance antenna 514 may also have multiple receive/transmit elements and the radio frequency system 108 may have multiple receive/transmit channels. For example if a parallel imaging technique such as SENSE is performed, the radio-frequency system 108 could have multiple coil elements.

The radio frequency system 516 and the gradient controller 512 are shown as being connected to the hardware interface 124 of the computer system 128. The memory 128 is shown as containing pulse sequence commands 530 instead of control commands. The pulse sequence commands 530 are commands or data which may be converted into such commands which are used for controlling the operation of the magnetic resonance imaging system 502. The memory 128 is further shown as containing magnetic resonance imaging data 532 that was acquired by controlling the magnetic resonance imaging system with the pulse sequence commands 530.

The memory 128 is further shown as containing a magnetic resonance image 534 that was reconstructed from the magnetic resonance imaging data 532. As with the medical system 300 in FIG. 3 the motion state 136 may be used in different ways. For example, the motion state 136 may be used for gating the acquisition of the magnetic resonance imaging data 532 as well as being used in the reconstruction of the magnetic resonance image 534.

Figure 6:
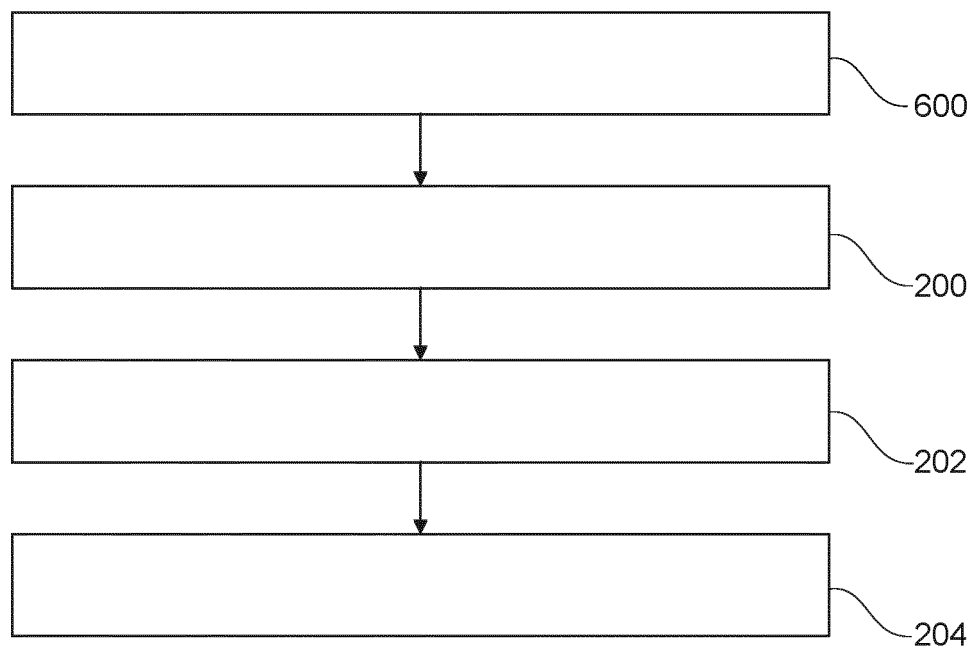
FIG. 6 shows a flow chart which illustrates a method of operating the medical system of FIG. 5.

FIG. 6 illustrates a method of controlling the medical system 500 of FIG. 5. First in step 600 the magnetic resonance imaging system 502 is controlled with the pulse sequence commands 530 to acquire the magnetic resonance imaging data 534. As step 600 is performed steps 200, 202, and 204 from FIG. 2 are simultaneously performed.

Figure 7:
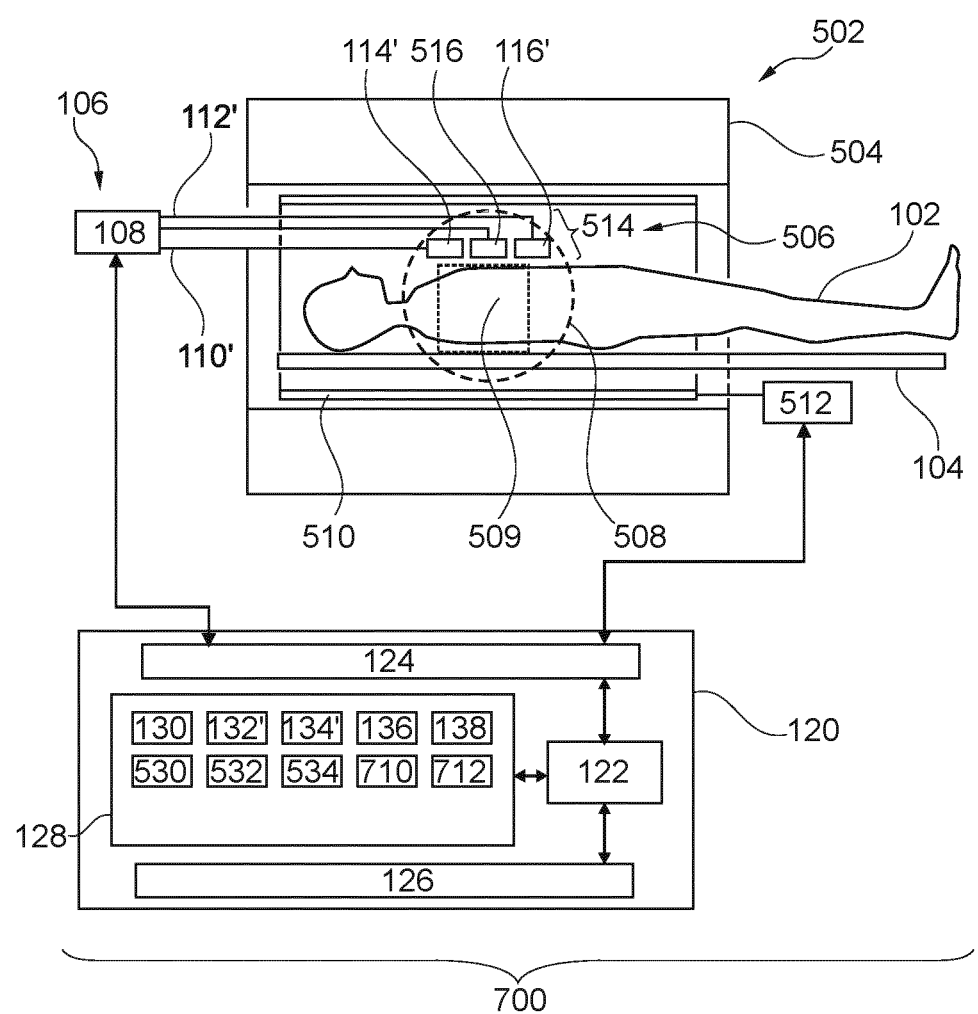
FIG. 7 illustrates a further example of a medical system.

FIG. 7 illustrates a further example of a medical system 700. The medical system in FIG. 7 is similar to that of FIG. 5. However, there are several changes. The multiple transmit coils 114 may also be at least one transmit coil 114'. The multiple receive coils may be at least one receive coil 116'. Likewise, the multiple receive channels may be at least one receive channel 112' and the multiple transmit coils may be at least one transmit coil 114'.

The memory 128 may further comprise a time-dependent gradient pulse frequency 710 that was determined from the pulse sequence commands 530. The motion state 136 may be compared with the time-dependent gradient pulse frequency 710 to determine if there is peripheral nerve stimulation in the subject 102. If the motion state correlates above a certain degree or above a certain amplitude within the same frequency range as motion detected, there may be a peripheral nerve stimulation warning signal 712 that is generated.

Figure 8:
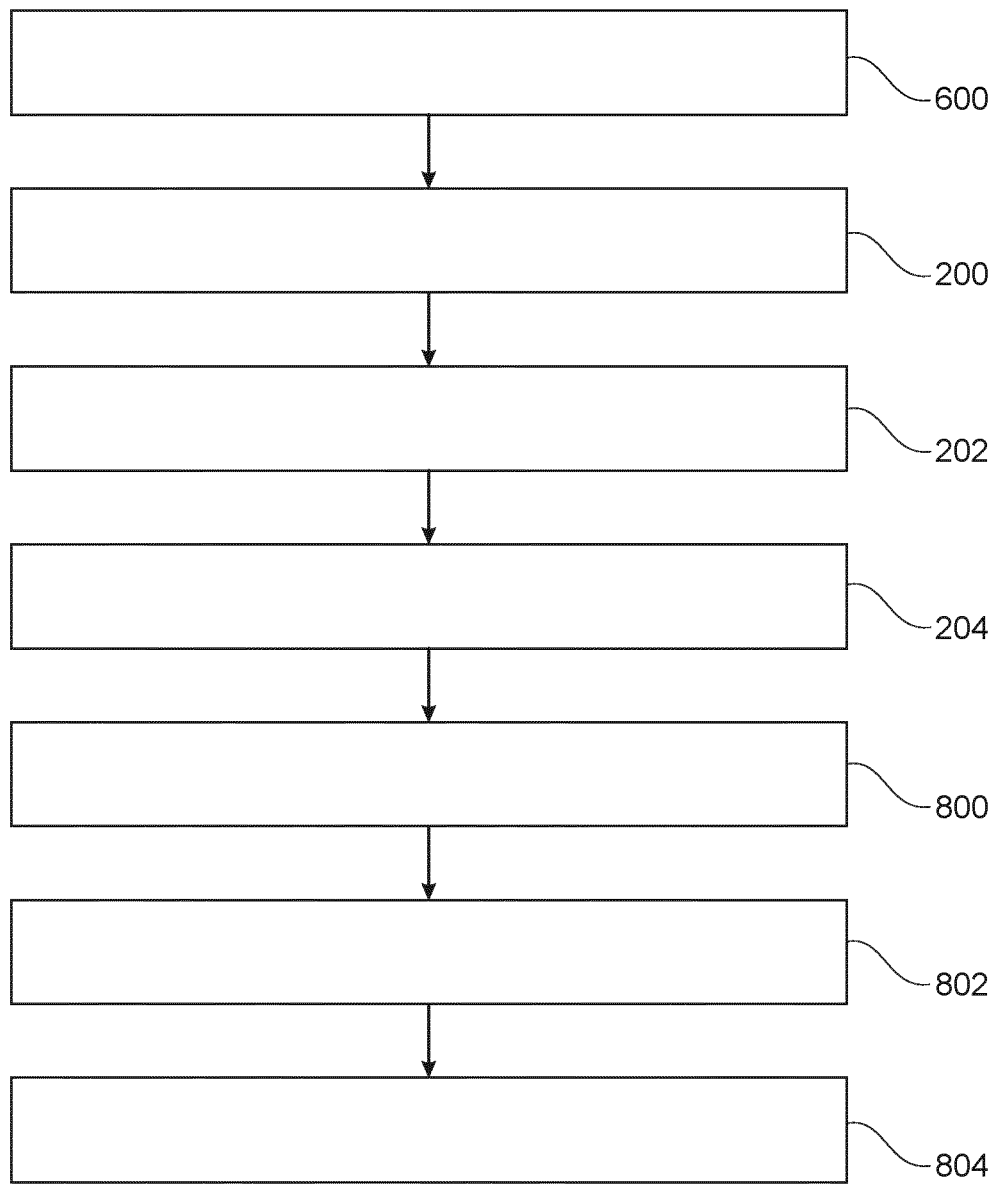
FIG. 8 shows a flow chart which illustrates a method of operating the medical system of FIG. 5.

FIG. 8 shows a flowchart which illustrates a method of operating the medical system 700 of FIG. 7. The method is similar to the method illustrated in FIG. 6. To start, steps 600, 200, 202, 204 are performed as in FIG. 6. After step 204 is performed or before step 800 is performed the time-dependent gradient pulse frequency 710 is determined using the pulse sequence commands 530. Next in step 802 subject motion with a periodicity within a predetermined range or correlation of the time-dependent gradient pulse frequency is detected using the motion state 136. For example, the motion state can be compared to the time-dependent gradient pulse frequency 710 or there can for example be a correlation that is calculated on the fly. Finally, in step 804 the peripheral nerve stimulation warning signal 712 is generated if the subject motion is detected.

Some examples may distributed pilot/reference signal in the coil array or antenna of a magnetic resonance imaging system. A fully digital pilot tone integration in the receive array. Optimal pilot signal is selected by Tx matrix and Rx matrix. Individual pilot tones can be different in frequency-phase-complex modulation.

For autonomous imaging this may enable ECG-free detection of heartbeats and separation and quantification of Head-Body Motion in combination with camera-based methods.

Both MRI and CT scans may need a number of input parameters and proper scan preparation. Depending on body size, body weight, patient position and anatomy to be scanned a protocol is chosen and modified to fit the patient. Typically, this data is entered manually. Physiology parameters (e.g. necessary for triggering scans) may be measured using dedicated sensors. It has been demonstrated recently, that relevant parameters can be deduced from live videostreams of a camera observing the patient during scanning.

During a MRI procedure the patient is covered by clothes and for the most applications covered by RF coils such as head and/or (anterior) surface coils. The Pilot Tone approach may be used as a contactless, electromagnetic navigator that offers monitoring of cardiac and respiratory motion independently of the acquisition.

Examples may have one or more of the following benefits:

ECG-free detection of heartbeats
Separation and Quantification of Head-Body Motion
Derive trigger for Cardiac and Respiratory Motion
Applications for MR LINAC-Radiotherapy Analytic optimization of dozens of in- and output parameters from RF sensors within the given timeframe is may be difficult considering the pure number of parameters and their non-linear (amplifier gain, fix parameter limits) interdependencies.

Camera based motion detection systems suffer from portioning issues in the tight bores of the current MR and CT scanners. On the other hand, single source/receiver pilot tone systems are only suitable to server one function. Patient variety and parameter demands makes it hard to optimize the single pilot tone system.

Signal-to-noise ration depends on position of pilot tone antenna/coil. In experiments, it was determined that multiple channels may be beneficial for extracting different types and directions of head motion, there is a need for multi-pilot tone sources distributed around the head/subject. Using multiple channels may provide one or more of the following features or benefits:

fixed frequency crystal oscillator
Extra component
Localization of pilot transmitter
Application limited for cardiac sensing/breathing
Workflow: extra step for workflow
Battery need to be recharged, replaced
Optimal reflection and motion signal depends on frequency
Signal depends on motion body
Selection of optimal frequency is important
Motion of organs (respiration)
Motion of body and extremities Using multiple channels may also enable measurement of one or more of the following:

Electrical parameters (permittivity and loading)
Coil loading condition

Examples may provide for a distributed pilot/reference signal in the coil array. A fully digital pilot tone integration in the receive array. This for example, may provide for an optimal pilot signal is selected by Tx matrix and Rx matrix. Individual pilot tones can be different in frequency-phase-complex modulation. By filtering and post-processing, the measured data, it is possible to detect and distinguish between different types of motion even allowing a localization of the movement. By using N receive coil elements in combination with M local transmitters; we obtain N×M signals at the same time. This allows to derive motion vectors.

By a fully digital local transmitter, the individual pilot tones may be separated by signal processing (e.g. via the code-division multiple access technique CDMA). Thus, full parallel pilot tone (multi-channel pilot tone signal) is feasible, including reconstruction of low resolution images and application for multiband MRI.

Figure 9:
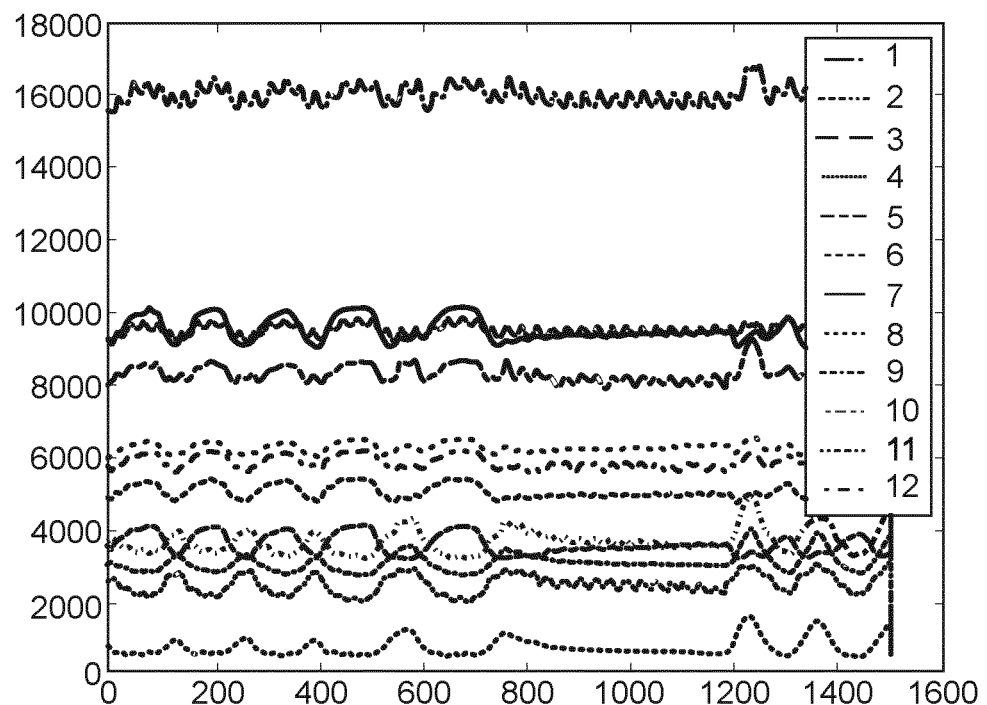
FIG. 9 shows an example of a multi-channel pilot tone data.

FIG. 9 illustrates an example of multi-channel pilot tone data 134. The plot shown in 134 shows a number of plots of individual pilot tone signals that were measured. Cardiac signals and breathing motion is well detected, but strongly depends upon individual coil channel as to how strong the cardiac or breathing signal is in each one individually.

Local coils can receive the narrow band signals, located outside the image band (pilot tone). Here the frequency is close to the MR frequency. By using additional RF channels, we integrate broadband receive antennas (or different frequency) in the MR coil. These additional RF channels receive motion modulated (amplitude &phase) signals on selected frequencies optimal for motion detection.

The data (multi-channel pilot tone data) can also feed a convolution neuronal network or a recurrent neuronal network. A recurrent neural network (RNN) is a class of artificial neural network where connections between nodes form a directed graph along a sequence. This allows it to exhibit dynamic temporal behavior for a time sequence. Unlike feedforward neural networks, RNNs can use their internal state (memory) to process sequences of inputs (here different frequencies). This makes them applicable to tasks such as unsegmented, connected motion recognition or pilot tone motion recognition.

Figure 10:
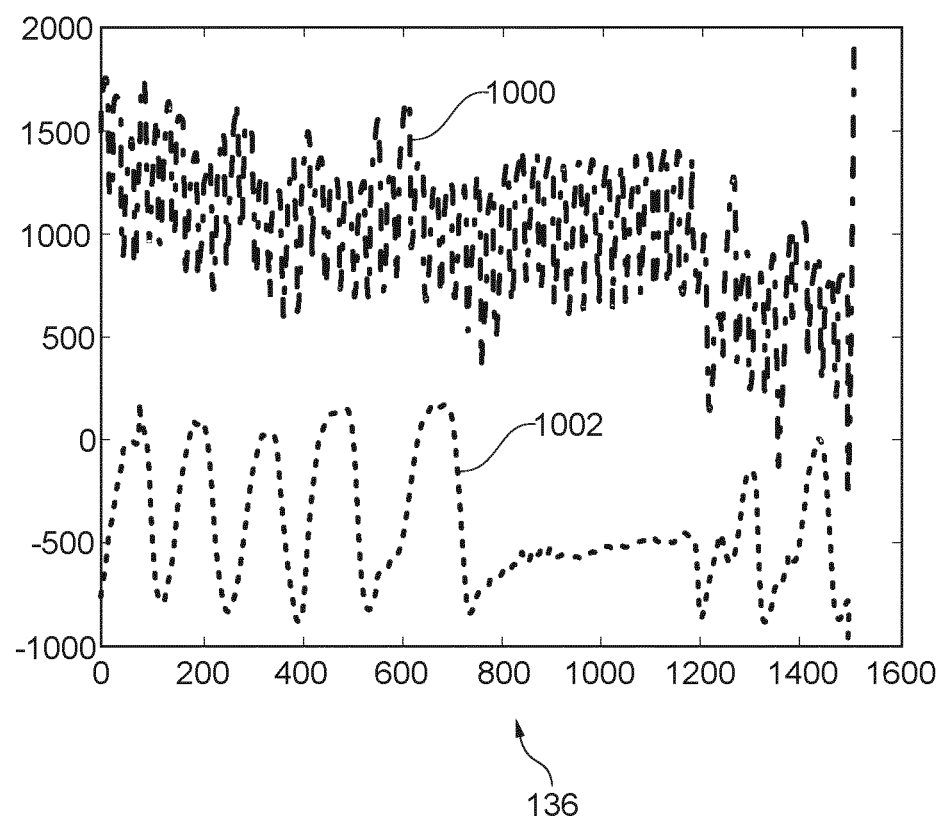
FIG. 10 shows an example of a motion state derived from the multi-channel pilot tone data of FIG. 9.

FIG. 10 illustrates an example of a motion state 136 that was determined from the multi-channel pilot tone signals 134 in FIG. 9. Shown in this plot is a synthesized cardiac signal 1000 and a synthesized breathing signal 1002.

Figure 11:
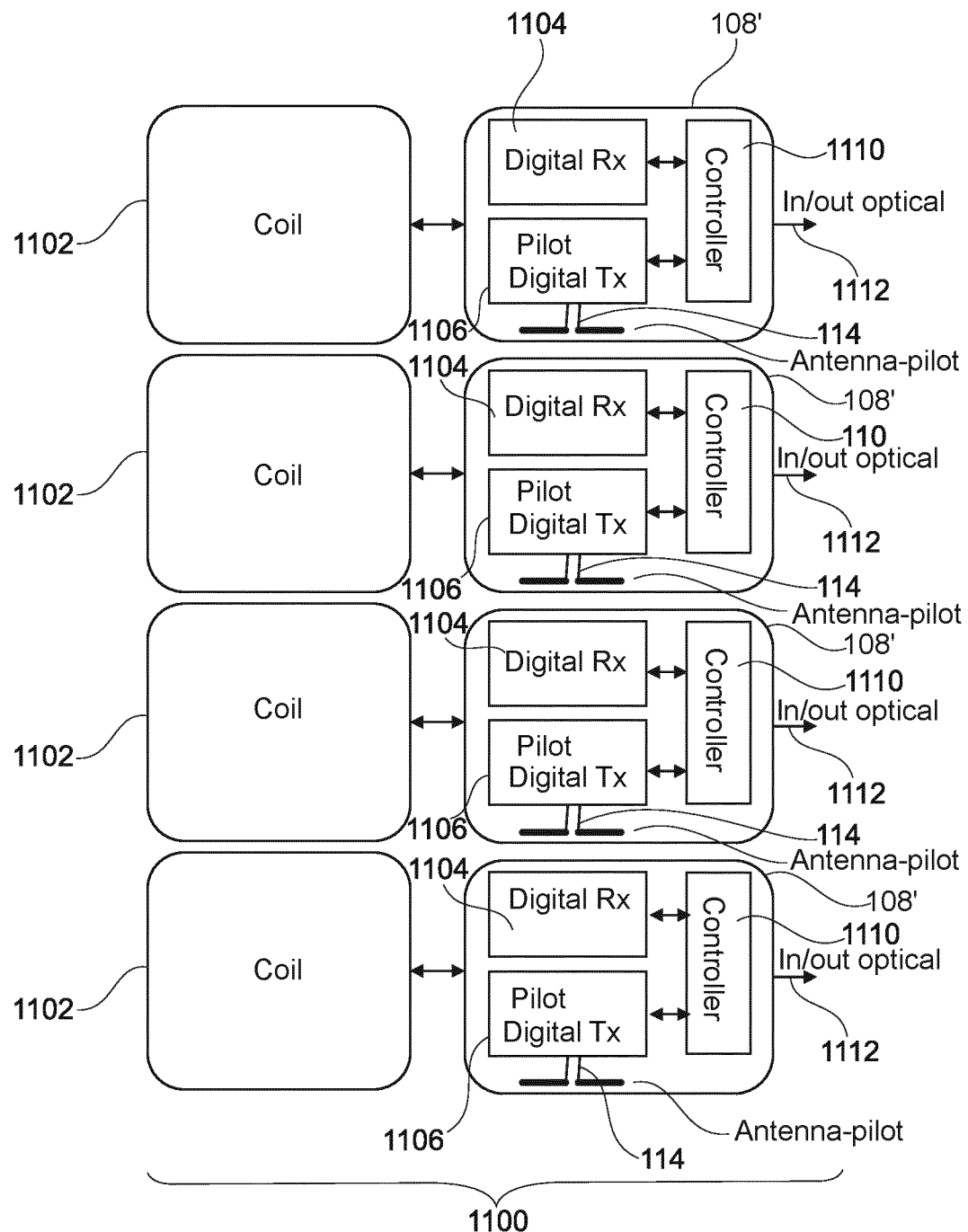
FIG. 11 illustrates an example of a combined MRI and pilot tone coil.

FIG. 11 illustrates an example of a combined magnetic resonance and pilot tone coil system 1100. The antenna 1100 comprises a number of coil elements 1102. The coil elements in this Fig. function as both the receive coil of the magnetic resonance imaging system as well as the multiple receive coils 116. The coils are connected to individual radio-frequency systems 108'. There is a radio-frequency system 108' for each channel in this example. The coil elements 1102 are each connected to a digital receive unit 1104. The digital receive unit is connected to a controller 1110 that is able to communicate with the rest of the magnetic resonance imaging system via an optical communication system 1112. The controller 1110 is also connected to a pilot tone digital transmitter 1106. The pilot tone digital transmitter is connected to the individual multiple transmit coils 114. The unique pilot tone signals are transmitted on the multiple transmit coils 114. The pilot tone data is then received by the coils 1102. Each digital pilot Tx may have a local antenna (stripline, dielectric).

FIG. 11 shows distributed digital pilot tone transceiver array. Each pilot antenna is decoupled with local MRI coil to obtain max. decoupling to prevent saturation of the preamplifier. Alternatively, the pilot tone is injected in the MR preamplifier with antiphase to prevent saturation. Avoiding preamp saturation is performed in the analogue domain. For multiband MRI the pilot tone may transmitted at individual frequencies and/or encoded.

The individual transmitter can be at a higher frequency then the MRI frequency. The undersampled signal is back-folded in the image domain and further processed.

Figure 12:
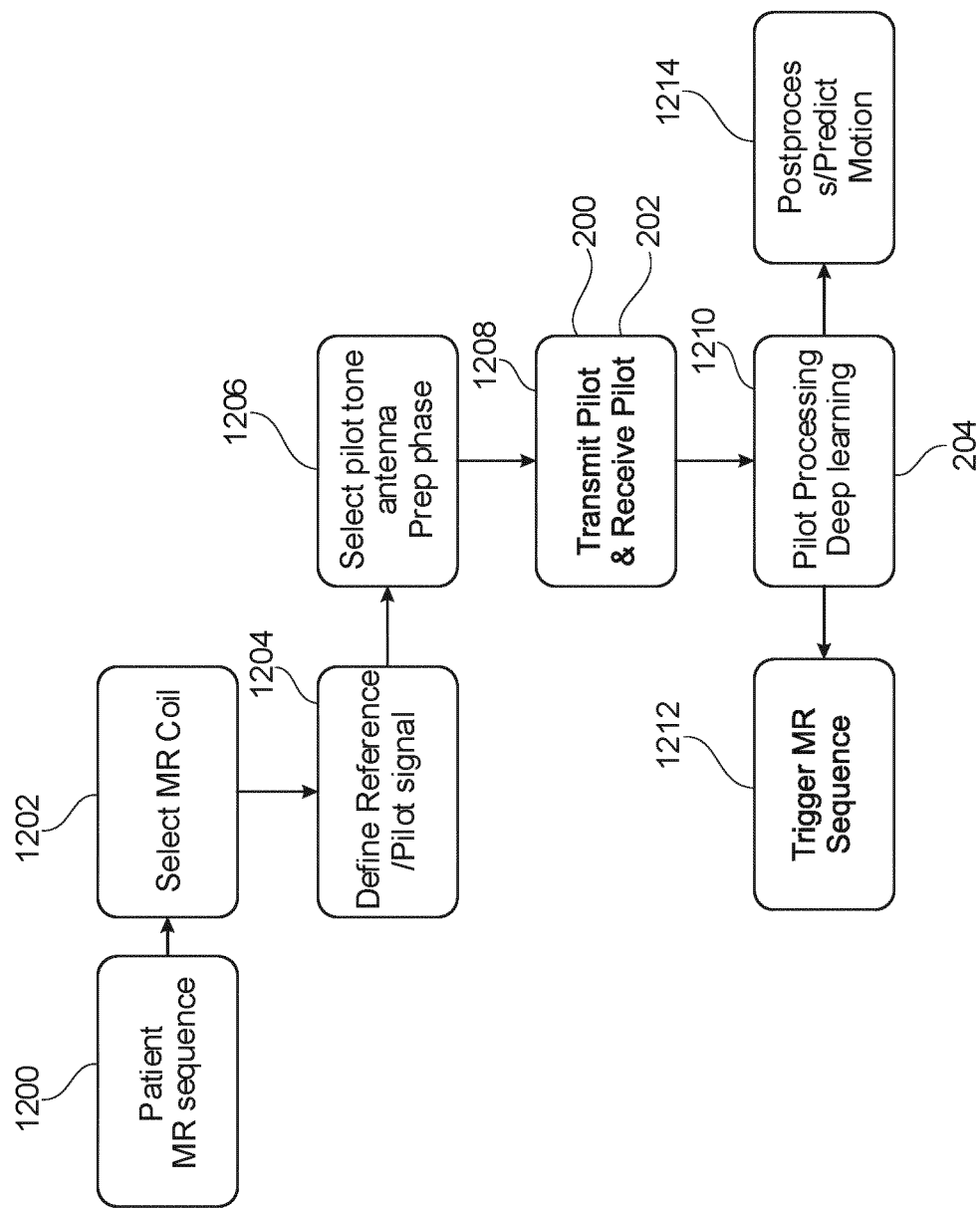
FIG. 12 illustrates an example of software system for a medical system.

FIG. 12 shows a flowchart which illustrates a method of operating the medical systems 500 and 700 of FIGS. 5 and 7. First in step 1200 a patient magnetic resonance sequence is selected/received. Next in step 1202 a magnetic resonance imaging coil is selected. In step 1204 the reference and pilot signals are defined. Then in step 1204 a pilot tone antenna is selected and there is a preparation phase. For example, if the pilot tone antenna is integrated into a magnetic resonance imaging antenna, this may be placed or positioned on the subject.

Then in step 1208 the pilot tone signals are transmitted and received. This is equivalent to steps 200 and 202. Then in step 1210 there are signaling processing of the pilot tone data to determine the motion state. This for example can be performed using signal processing or using deep learning or other neural networks. This may be equivalent to step 204. After step 1210 two independent steps can be performed. In step 1212 the motion state is used to trigger the magnetic resonance imaging sequence. For example, the magnetic resonance imaging may be triggered at a particular breathing or cardiac phase. After step 1210 step 1214 may also be performed. In this step the motion state is used for processing of the magnetic resonance imaging data or either for predicting the motion of the subject and may be used for either correcting the image afterwards or correcting the acquisition in a predictive factor to improve the quality.

For the distributed Pilot tone, the MRI system can define the optimal location of transmitter and receiver for highest pilot signal sensitivity as shown in FIG. 12. Pilot tones are sent simultaneously. Decoding is performed by individual modulation of individual transmitters.

Another application is the detection of Peripheral Nerve Stimulation during magnetic resonance imaging. It is possible to use the pilot tone signals acquired by the receive coil array and correlate it with gradient waveform signal to detect and trigger for PNS detection. The full matrix of the receive coil is measured and correlated with the gradient waveform to detect PNS.

If certain thresholds are reached, the MR sequence is adapted to reduce PNS. The sequence automatically adapts for patient comfortable parameters. Measure: change readout direction, change sequence, gradient strength, reposition patient. The data (multi-channel pilot tone data) can also feed a convolution neuronal network or a recurrent neuronal network.

Strong gradients applied during MRI exams can trigger peripheral nerve stimulation resulting in motion of muscle fibers or whole muscles.

The PNS . . .
 Is discomfort for patient
 level is individual for patient
 Limits are set globally, disregarding individual sensitivity for PNS
 Cannot be communicated by Patients with handicap or sedation. There is no quantitative feedback for operator, cannot be detected by camera-based methods
 Can induce MR artefact due to motion
 Can lead to an unintended scan about, when the patient calls the operators due PNS may be detected by using the pilot tone signals acquired by the receive coil array for PNS detection.

In general, PNS induced effects on the Pilot tone signals are expected to be lower than that of e.g. breathing. Due to this, and to distinguish from other motion the Pilot tone signals acquired by the receive coil may be correlated with the gradient waveform.

If certain thresholds are reached, the MR sequence is adapted to reduce PNS. The sequence automatically adapts for patient comfortable parameters. Possible measures are to change
 change readout direction,
 change sequence,
 gradient strength,
 position/pose of patient Additional supplementary data may also be used such as optical, camera, radar, and ultrasonic acoustic detection.

Current MRI scanners feature a low-power transmit path independent from the transmit chain of the body coil for calibration purposes. Here, a small off-resonant coil is attached to the RF screen to the body coil. The transmit power for this coil was adjusted so that RF signals are in the same order of that originating from the spin system. Standard MRI coils are used for reception.

Pilot tone measurements can be interleaved or merged with the MR sequence. Tests showed that this setup allows to detect motion induced by breathing. Further tests were performed to increase the sensitivity of the set-up.

The FIG. 9 above shows an example of pilot tone magnitude signals. Additional information can be gained when simultaneously observing the phase of the acquired signals. The ideal position of the off-resonant coil was determined in tests to provide most sensitive outcome for breathing and heart motion. In the given experiments, the best setup was to place the coil on top of the patient's sternum. The acquisition of the pilot tone using all available RX coils allows for (limited) spatial sensitivity.

This insight can be used to distinguish different motion types.

It is likely that for PNS detection another position is more suitable, e.g., close to the long muscles of the patients back.

The data (multi-channel pilot tone data) can also feed a convolution neuronal network or a recurrent neuronal network. A recurrent neural network (RNN) is a class of artificial neural network where connections between nodes form a directed graph along a sequence. This allows it to exhibit dynamic temporal behavior for a time sequence. Unlike feedforward neural networks, RNNs can use their internal state (memory) to process sequences of inputs (here different frequencies). This makes them applicable to tasks such as unsegmented, connected motion recognition or camera motion recognition (see FIG. 13 below).

Figure 13:
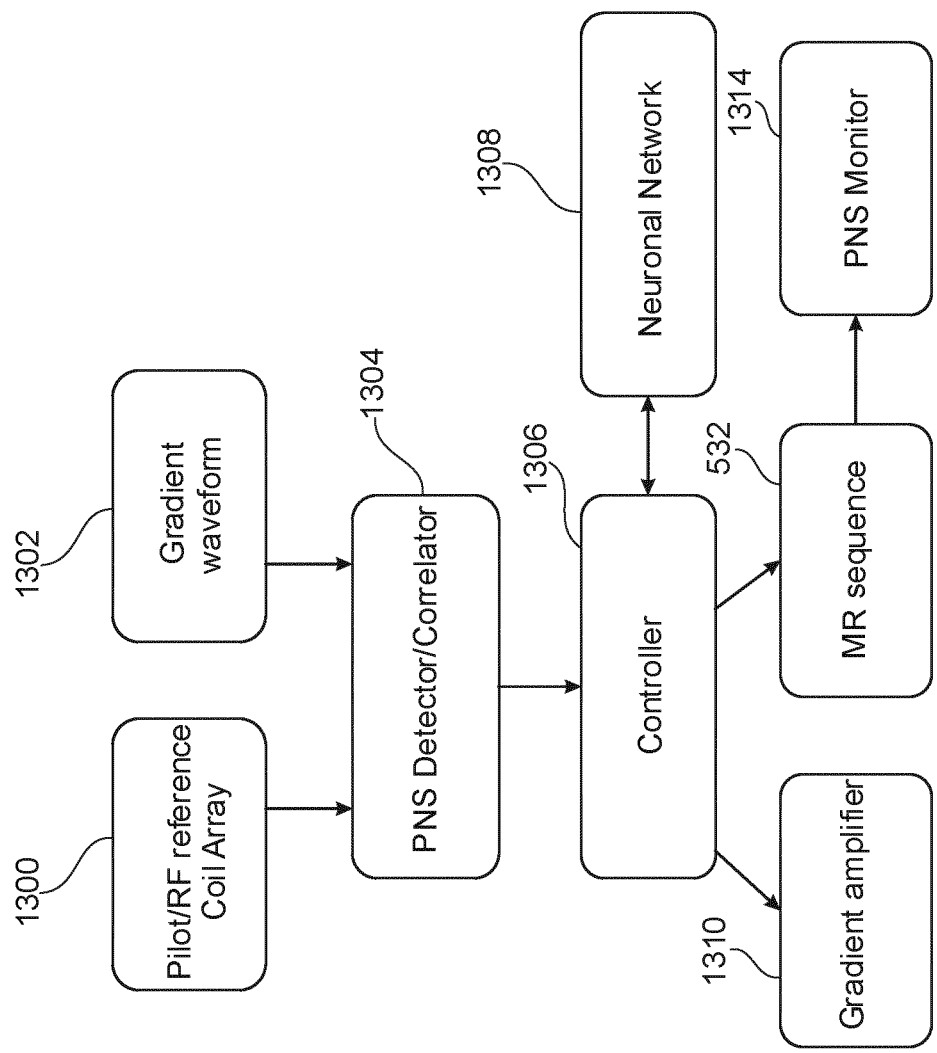
FIG. 13 illustrates a further example of software system for a medical system.

FIG. 13 illustrates a software algorithm and functional building blocks of a system that may for example be incorporated into a magnetic resonance imaging system such as the medical system 700 illustrated in FIG. 7. Block 1300 represents the pilot tone system and the radio-frequency reference coil array. Block 1302 represents the gradient waveform from the pulse sequence commands. Block 1304 represents a software component that is a peripheral nerve stimulation detector and/or correlator 1304. The detector or correlator 1304 is able to take information about the gradient waveform 1302 and information from the pilot tone data 1300 to detect if there is peripheral nerve stimulation. This is then fed into the controller 1306.

For example, the controller 1306 may be equivalent to the processor 122. This information could then be forwarded or processed from the controller and fed to a neural network 1308 that may for example be equivalent to the neural network 138. The controller 1306 can use a detection of the peripheral nerve stimulation for example to modify behavior of the gradient amplifier 1310, and possibly even modify the behavior or change the pulse sequence commands 530. This data may also be provided to a peripheral nerve stimulation monitor 1314. This for example may be provided via the user interface 126.

The following scheme illustrated in FIG. 13 shows how the Pilot Tone data shall be processed and used.

In a first step the Pilot Tone data is correlated with the gradient waveforms. Depending on the level of signal correlation the controller decides: correlation below first threshold=no low PNS: run the sequence as planned correlation below second threshold=considerable PNS: adapt sequence correlation above second threshold=PNS at pain limit or considerable image artefacts expected: terminate scan by gradient amplifier interlock While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical system
102 subject
104 subject support
106 pilot tone system
108 radio frequency system
108' individual radio frequency system
110 multiple transmit channels
110' at least one transmit channel
112 multiple receive channels
112' at least one receive channel
114 multiple transmit coils
114' at least one transmit coil
116 multiple receive coils
116' at least one receive coil
120 computer
122 processor
124 hardware interface
126 user interface
128 memory
130 machine executable instructions
132 uniques pilot tone signals
132' one or more pilot tone signals
134 multi-channel pilot tone data
134' pilot tone data
136 motion state
138 recurrent neural network
200 transmit multi-channel pilot tone signals by controlling at least a portion of the multiple transmit channels to transmit the unique pilot tone signals
202 acquire multi-channel pilot tone data by controlling at least a portion of the multiple receive channels to receive the multi-channel pilot tone data
204 determine a motion state of the subject using the multi-channel pilot tone data
300 medical system
302 tomographic imaging system
304 imaging zone
310 control commands
312 tomographic imaging data
314 tomographic medical image
400 acquire tomographic imaging data from a subject within an imaging zone
500 medical imaging system
502 magnetic resonance imaging system
504 magnet
506 bore of magnet
508 imaging zone
509 region of interest
510 magnetic field gradient coils
512 magnetic field gradient coil power supply
514 magnetic resonance antenna
516 radio-frequency coil
530 pulse sequence commands
532 magnetic resonance imaging data
534 magnetic resonance image
600 acquire magnetic resonance imaging data
700 medical system
710 time dependent gradient pulse frequency
712 peripheral nerve stimulation warning signal
800 determine a current gradient pulse frequency using the pulse sequence commands
802 detect subject motion with a periodicity within a predetermined range of the current gradient pulse frequency using the pilot tone data
804 provide a peripheral nerve stimulation warning signal if the subject motion is detected
1000 synthesized cardiac signal
1002 synthesized breathing signal
1100 combined MR and pilot tone coil
1102 coil
1104 Digital Rx
1106 pilot tone digital Tx
1108 antenna pilot tone
1110 controller
1112 optical communication

The invention claimed is:
1. A medical system comprising:
a memory storing machine executable instructions;
a processor configured for controlling the medical system; and
a pilot tone system;
wherein the pilot tone system comprises:
a radio frequency system comprising multiple transmit channels and multiple receive channels, wherein the multiple transmit channels are configured for each transmitting unique pilot tone signals via multiple transmit coils wherein the multiple receive channels are configured for receiving multi-channel pilot tone data via multiple receive coils;
wherein execution of the machine executable instructions causes the processor to:

transmit multi-channel pilot tone signals by controlling at least a portion of the multiple transmit channels to transmit the unique pilot tone signals;
acquire multi-channel pilot tone data due to impedance response to the transmitted pilot tone signals by controlling at least a portion of the multiple receive channels to receive the multi-channel pilot tone data; and
determine a motion state of the subject using the multi-channel pilot tone data.

2. The medical system of claim 1, wherein the radio frequency system is configured for encoding each of the unique pilot tone signals using any one of the following: frequency encoding, phase encoding, complex modulating, CDMA encoding, and combinations thereof.

3. The medical system of claim 1, wherein the motion state is at least one of the following:
subject motion location;
a motion vector;
a subject motion classification;
a breathing state;
a heart motion state;
a translation vector descriptive of at least a portion of the subject; or
a rotation descriptive of at least a portion of the subject.

4. The medical system of claim 1, wherein execution of the machine executable instructions causes the processor to determine the motion state by at least one of the following:
using a recurrent neural network configured for receiving the multi-channel pilot tone data and the unique pilot tone signals and for outputting the motion state;
detecting a distance between the subject and each of the multiple receive coils;
using digital filtering; or
using principal component analysis.

5. The medical system of claim 1, wherein the medical system further comprises a magnetic resonance imaging system, wherein the individual receive channels include (i) one of the multiple receive coils configured as a magnetic resonance imaging coil and (ii) a radio frequency system including one of the multiple pilot tone transmit coils, the magnetic resonance imaging coil being decoupled from the pilot tone transmit coil within the individual receiver channel.

6. The medical system of claim 5, wherein the radio frequency system includes a digital receiver coupled to the magnetic resonance imaging coil and a pilot tone digital transmitter coupled to the pilot tone transmit coil.

7. The medical system of claim 5, wherein the magnetic resonance imaging system is configured for acquiring magnetic resonance imaging data within an imaging frequency range, wherein the multiple transmit channels are configured for transmitting the unique pilot tone signals outside of the imaging frequency range.

8. The medical system of claim 7, wherein the memory further contains pulse sequence commands configured for controlling the magnetic resonance imaging system to acquire magnetic resonance imaging data, wherein execution of the machine executable instructions further cause the processor to control the magnetic resonance imaging system with the pulse sequence commands to acquire the magnetic resonance imaging data, wherein execution of the machine executable instructions causes the processor to perform the following during controlling the magnetic resonance imaging system with the pulse sequence commands:
transmit the multi-channel pilot tone signals;
acquire the multi-channel pilot tone data; and
determine the motion state of the subject using the multi-channel pilot tone data.

9. The medical system of claim 8, wherein execution of the machine executable instructions further causes the processor to:
determine a current gradient pulse frequency using the pulse sequence commands;
detect subject motion with a periodicity within a predetermined range of the current gradient pulse frequency using the motion state; and
provide a peripheral nerve stimulation warning signal if the subject motion is detected.

10. The medical system of claim 9, wherein execution of the machine executable instructions further causes the processor to perform any one of the following if the peripheral nerve stimulation warning signal is provided:
select alternative pulse sequence commands;
modify the pulse sequence commands; and
cancel execution of the pulse sequence commands.

11. The medical system of claim 1, wherein the pilot tone system further comprises the multiple transmit coils and the multiple receive coils; wherein the medical system further comprises a tomographic imaging system for acquiring tomographic imaging data from a subject within an imaging zone, where execution of the machine executable instructions further causes the processor to control the tomographic imaging system to acquire the tomographic imaging data; wherein execution of the machine executable instructions causes the processor to perform the following during controlling the tomographic imaging system to acquire the tomographic imaging data:
transmit the multi-channel pilot tone signals;
acquire the multi-channel pilot tone data; and
determine the motion state of the subject using the multi-channel pilot tone data.

12. The medical system of claim 11, wherein execution of the machine executable instructions further causer the processor to:
reconstruct a medical image using the tomographic imaging data; and
correct the reconstruction of the medical image using the motion state of the subject.

13. The medical system of claim 11, wherein the tomographic imaging system is any one of the following: a positron emission tomography system, a single photon emission tomography system, and an X-ray computed tomography system.

14. The medical system of claim 1, wherein the pilot tone signals are continuous wave signals.

15. A computer program product comprising machine executable instructions for execution by a processor controlling a medical system wherein the medical system comprises a pilot tone system, wherein the pilot tone system comprises a radio frequency system comprising multiple transmit channels and multiple receive channels, wherein the multiple transmit channels are configured for each transmitting unique pilot tone signals via multiple transmit coils, wherein the multiple receive channels are configured for receiving multi-channel pilot tone data via multiple receive coils,
wherein execution of the machine executable instructions causes the processor to:
transmit multi-channel pilot tone signals by controlling at least a portion of the multiple transmit channels to transmit the unique pilot tone signals;
acquire multi-channel pilot tone data due to impedance response to the transmitted pilot tone signals by controlling at least a portion of the multiple receive channels to receive the multi-channel pilot tone data; and determine a motion state of the subject using the multi-channel pilot tone data.

16. A method of operating a medical system, wherein the medical system comprises a pilot tone system, wherein the pilot tone system comprises a radio frequency system comprising multiple transmit channels and multiple receive channels, wherein the multiple transmit channels are configured for each transmitting unique pilot tone signals via multiple transmit coils, wherein the multiple receive channels are configured for receiving multi-channel pilot tone data via multiple receive coils, wherein the method comprises:

transmitting multi-channel pilot tone signals by controlling at least a portion of the multiple transmit channels to transmit the unique pilot tone signals;

acquiring multi-channel pilot tone data due to impedance response to the transmitted pilot tone signals by controlling at least a portion of the multiple receive channels to receive the multi-channel pilot tone data;

determining a motion state of the subject using the multi-channel pilot tone data.

17. The method of claim 16, wherein the pilot tone signals are continuous wave signals.

18. The method of claim 16, further comprising:

controlling the medical system with pulse sequence commands;

determining a current gradient pulse frequency using the pulse sequence commands;

detecting subject motion with a periodicity within a predetermined range of the current gradient pulse frequency using the motion state; and providing a peripheral nerve stimulation warning signal if the subject motion is detected.

19. The method of claim 18, further comprising performing any one of the following if the peripheral nerve stimulation warning signal is provided:

selecting alternative pulse sequence commands;

modifying the pulse sequence commands; and canceling execution of the pulse sequence commands.

* * * * *